United States Patent
Liu et al.

(10) Patent No.: US 9,445,744 B2
(45) Date of Patent: Sep. 20, 2016

(54) METHODS, SYSTEMS, AND DEVICES FOR SPINE CENTRUM EXTRACTION AND INTERVERTEBRAL DISK DIVIDING

(71) Applicant: SHENZHEN MINDRAY BIO-MEDICAL ELECTRONICS CO., LTD., Shenzhen (CN)

(72) Inventors: Yan Liu, Shenzhen (CN); Xiaoyun Deng, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 242 days.

(21) Appl. No.: 14/041,919

(22) Filed: Sep. 30, 2013

(65) Prior Publication Data

US 2014/0046169 A1    Feb. 13, 2014

Related U.S. Application Data

(63) Continuation of application No. PCT/CN2012/073131, filed on Mar. 27, 2012.

(30) Foreign Application Priority Data

Mar. 31, 2011    (CN) .......................... 2011 1 0080865

(51) Int. Cl.
*A61B 5/05* (2006.01)
*A61B 5/055* (2006.01)
*G06T 7/00* (2006.01)
*A61B 5/00* (2006.01)

(52) U.S. Cl.
CPC ............ *A61B 5/055* (2013.01); *G06T 7/0042* (2013.01); *G06T 7/0081* (2013.01); *A61B 5/4566* (2013.01); *G06T 2207/10088* (2013.01); *G06T 2207/20141* (2013.01); *G06T 2207/20156* (2013.01); *G06T 2207/30012* (2013.01); *G06T 2207/30172* (2013.01)

(58) Field of Classification Search
CPC ..... A61B 5/005; A61B 5/4566; A61B 6/505
See application file for complete search history.

(56) References Cited

U.S. PATENT DOCUMENTS

| | | | |
|---|---|---|---|
| 6,490,472 B1 | 12/2002 | Li et al. | |
| 7,876,938 B2* | 1/2011 | Huang | G06T 7/0028 382/128 |
| 8,014,575 B2* | 9/2011 | Weiss | B60R 25/00 382/128 |
| 2007/0276214 A1* | 11/2007 | Dachille | G06T 7/0012 600/407 |
| 2012/0143090 A1* | 6/2012 | Hay | A61B 6/505 600/587 |
| 2013/0060146 A1* | 3/2013 | Yang | G01B 11/245 600/476 |

FOREIGN PATENT DOCUMENTS

| | | |
|---|---|---|
| CN | 1449721 A | 10/2003 |
| CN | 101301224 A | 11/2008 |
| CN | 101515367 A | 8/2009 |
| JP | 2000126150 A | 5/2000 |

* cited by examiner

*Primary Examiner* — Joel Lamprecht
(74) *Attorney, Agent, or Firm* — Kory D. Christensen; Stoel Rives LLP

(57) ABSTRACT

Devices, systems, and methods for spine centrum extraction and intervertebral disk dividing are disclosed.

20 Claims, 13 Drawing Sheets

METHODS, SYSTEMS, AND DEVICES FOR SPINE CENTRUM EXTRACTION AND INTERVERTEBRAL DISK DIVIDING

TECHNICAL FIELD

This disclosure relates to a magnetic resonance imaging system and more particularly to spine centrum and intervertebral disk dividing methods and systems using magnetic resonance imaging.

DETAILED DESCRIPTION

Figure 1:
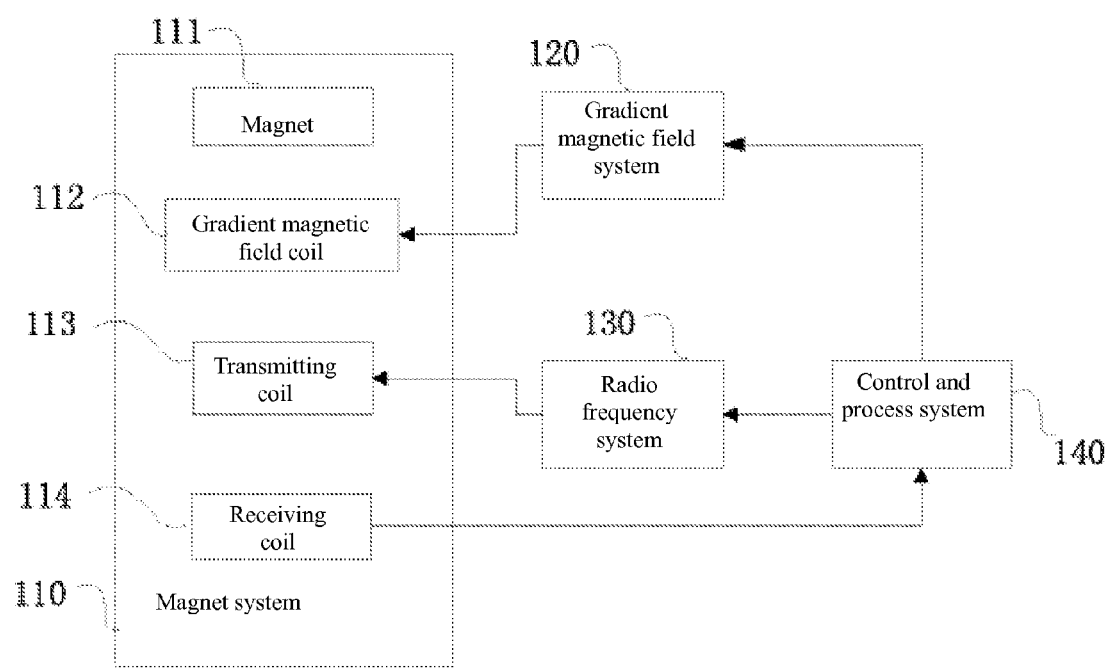
FIG. 1 is a structural diagram for an embodiment of a magnetic resonance imaging system.

Magnetic resonance imaging (MRI) examination has become increasingly popular due to the fact that it causes no damage and provides for free section and multi-parameter imaging. In recent years, it has shown great promise in clinical applications involving the spine.

A typical MRI scanning process on a spine intervertebral disk is described as follows. A group of scan lines is positioned on a diseased intervertebral disk on a sagittal scout image by a doctor or a technician. The position and the angle of the line group need to be adjusted repeatedly so that the line group is ensured to pass through the center of the intervertebral disk, which results in complicated and time-consuming positioning and adjustment processes. For these reasons, an intelligent scanning and positioning method for the intervertebral disk can be realized in the event that MRI is capable of extracting the spine intervertebral disk automatically.

Automatic extraction of the intervertebral disk can be achieved by an image processing method as follows. The centrum of the intervertebral disk is automatically divided or recognized on a sagittal image. When dividing the intervertebral disk by a traditional image segmentation method, the differences of gray scale between the centrum and the intervertebral disk are used. For example, the centrum is white, while the intervertebral disk is black on a T1-weighted image, although this is not absolute. Under the influence of different weights, such differences of gray scale may always become unapparent for the centrum and the intervertebral disk, and an inverse intervertebral disk may even be present on a T2- or STIR-weighted image. It is therefore difficult to fully apply the traditional methods in this circumstance. Of course, the centrum can also be extracted by deformable model matching. However, the number of the visible centrum in a spine image does not remain unchanged, and thus the matching may become ineffective when there are too many or too few visible centrums. Some other dividing methods require interactive operations, such as the selection of characteristic points by doctors or technicians, which impacts efficiency.

According to one aspect of the disclosure, a spine centrum extracting method includes positioning a spinal cord line by using magnetic resonance image data; determining a centrum axis section according to the spinal cord line; positioning a seed point within the centrum according to the centrum axis section; and extracting a centrum region on the basis of the seed point within the centrum by using seed region growth.

According to another aspect of the disclosure, a spine centrum extracting device includes a spinal cord line positioning unit configured for positioning a spinal cord line by using magnetic resonance image data; an axis section determining unit configured for determining a centrum axis section according to the spinal cord line; a seed point positioning unit configured for positioning a seed point within the centrum according to the centrum axis section; and a centrum region extracting unit configured for extracting a centrum region on the basis of the seed point within the centrum by using seed region growth.

According to still another aspect of the disclosure, a spine intervertebral disk dividing method includes positioning a spinal cord line by using magnetic resonance image data; determining a centrum axis section according to the spinal cord line; positioning a seed point within the centrum according to the centrum axis section; extracting a centrum region on the basis of the seed point within the centrum by using seed region growth; positioning a vertex of the centrum region on the extracted centrum region; calculating a central point of two opposite sides of the intervertebral disk by using the vertices of two adjacent centrum regions; and determining an intervertebral disk central line according to the central point of the two opposite sides.

According to yet another aspect of this disclosure, a spine intervertebral disk dividing device includes a spinal cord line positioning unit configured for positioning a spinal cord line by using magnetic resonance image data; an axis section determining unit configured for determining a centrum axis section according to the spinal cord line; a seed point positioning unit configured for positioning a seed point within the centrum according to the centrum axis section; a centrum region extracting unit configured for extracting a centrum region on the basis of the seed point within the centrum by using seed region growth; a centrum region vertex positioning unit configured for positioning a vertex of the centrum region on the extracted centrum region; an intervertebral disk central point positioning unit configured for calculating a central point of two opposite sides of the intervertebral disk by using the vertices of two adjacent centrum regions; and an intervertebral disk central line determining unit configured for determining an intervertebral disk central line according to the central point of the two opposite sides.

In one embodiment, a magnetic resonance imaging system includes the above-mentioned spine intervertebral disk dividing device and/or spine centrum extracting device.

Self-adaptive extraction of the centrum and intervertebral disk is implemented in one embodiment based on various features including a uniform gray scale within the centrum, a fixed centrum shape and/or apparent boundary between the centrum and the intervertebral disk. The extraction results are neither affected by the inconsistent gray scale of the centrum or the intervertebral disk nor by the image weight. All centrums in the image can be extracted self-adaptively, and the location and the angle of each intervertebral disk central line can be calculated, which may be effectively applied to fully-automatic positioning of spine intervertebral disk scanning in a magnetic resonance image (MRI).

Referring to FIG. 1, a magnetic resonance imaging system 100 in one embodiment comprises a magnet system 110, a gradient magnetic field system 120, a radio frequency system 130, and a control and process system 140. The magnet system 110 may include a magnet 111, a gradient magnetic field coil 112, a transmitting coil 113, and a receiving coil 114. The magnet 111, which can be a permanent magnet or a normal conductive magnet, is operable to provide a subject to be tested (such as a patient) with a constant main field. The gradient magnetic field coil 112 is operable to generate a gradient magnetic field in a three-dimensional space. The transmitting coil 113 is operable to provide a radio frequency (RF) pulse to excite nuclear spin in the subject to be tested. The receiving coil 114 is operable to detect an echo signal emitting from the subject to be tested. The gradient magnetic field system 120 is in communication with the control and process system 140, and is operable to drive the gradient magnetic field coil 112 under the control of the control and process system 140. The radio frequency system 130 is in communication with the control and process system 140, and is operable to generate RF pulses and further apply an amplified RF pulse onto the transmitting coil 113 under the control of the control and process system 140.

In one embodiment, the control and process system 140 not only controls the respective parts of the imaging system but also processes the echo signal. The control and process system 140 may include a spine centrum extracting device 200, which is used to extract a spine centrum of the tested subject based on an obtained magnetic resonance image after the echo signal detected by the receiving coil 114 is delivered to the control and process system 140.

Figure 2:
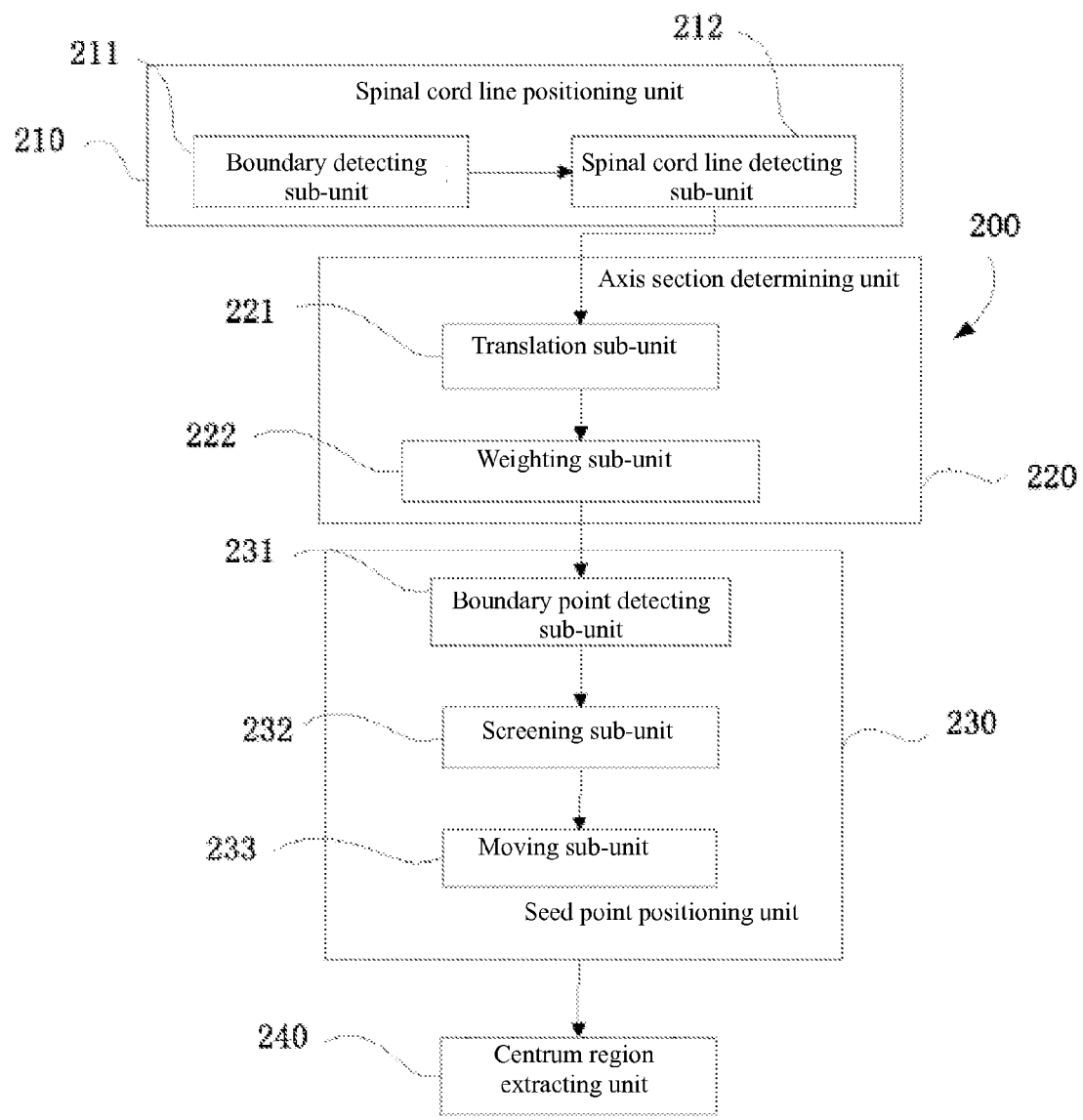
FIG. 2 is a structural diagram for a spine centrum extracting device.

In one embodiment, as shown in FIG. 2, the spine centrum extracting device 200 comprises a spinal cord line positioning unit 210, an axis section determining unit 220, a seed point positioning unit 230, and a centrum region extracting unit 240. The spinal cord line positioning unit 210 is configured for positioning a spinal cord line by using the magnetic resonance image data. The axis section determining unit 220 is configured for determining a centrum axis section according to the spinal cord line. The seed point positioning unit 230 is configured for positioning a seed point within the centrum according to the centrum axis section. The centrum region extracting unit 240 is configured for extracting a centrum region on the basis of the seed point within the centrum by using seed region growth. The aforementioned units, as well as the other units and sub-units described herein, may be implemented as hardware components, as software modules stored in a memory and executed by a processor, or as various combinations of hardware, software, and/or firmware known to those of skill in the art. Furthermore, the functionality of various units or sub-units may be combined or separated in various embodiments.

In one embodiment, based on the approximately uniform gray scale in the centrum, the spinal cord line positioning unit 210 extracts bilateral body boundaries of a tested subject (such as a human torso) and then detects the spinal cord line according to the distance defined by the bilateral body boundaries. The spinal cord line positioning unit 210 may include a boundary detecting sub-unit 211 and a spinal cord line detecting sub-unit 212. The former is operable to detect the bilateral body boundaries of the tested subject in a magnetic resonance image by using the transition feature between tissues of the tested subject and a background, while the latter is operable to detect the spinal cord line according to the tissue width of the tested subject defined by the body boundaries.

In another embodiment, on the basis that the spinal cord line and the centrum axis have a consistent trend and keep a close distance to each other, the axis section determining unit 220 first obtains a centrum axis and then gets an image of the centrum axis section according to the centrum axis. Thereafter, the seed point positioning unit 230 positions the seed point within the centrum according to the centrum axis section by adoption of an apparent boundary between the centrum and the intervertebral disk. The axis section determining unit 220 may include a translation sub-unit 221 and a weighting sub-unit 222. Herein, the former is operable to obtain plurality of centrum axes after translating the spinal cord line by multiple given translation distances, while the latter is operable to obtain the centrum axis section by performing a weighted sum of the gray scales of plurality of centrum axes. The seed point positioning unit 230 may include a boundary point detecting sub-unit 231, a screening sub-unit 232, and a moving sub-unit 233. The boundary point detecting unit 231 is operable to calculate the variation gradient of the gray scale on the centrum axis section and take the point at which the gradient value is larger than a given threshold as a candidate boundary point of the centrum and the adjacent intervertebral disk. The screening sub-unit 232 is operable to screen the detected candidate boundary point in accordance with a predetermined rule, such as a third predetermined rule mentioned hereafter, to obtain the boundary point of the centrum and the adjacent intervertebral disk. The moving sub-unit 233 is operable to move the coordinate of the boundary point by a predetermined value along a centrum axis direction. Thereafter, the point corresponding to the obtained new coordinate is marked as the seed point within the centrum.

Figure 3:
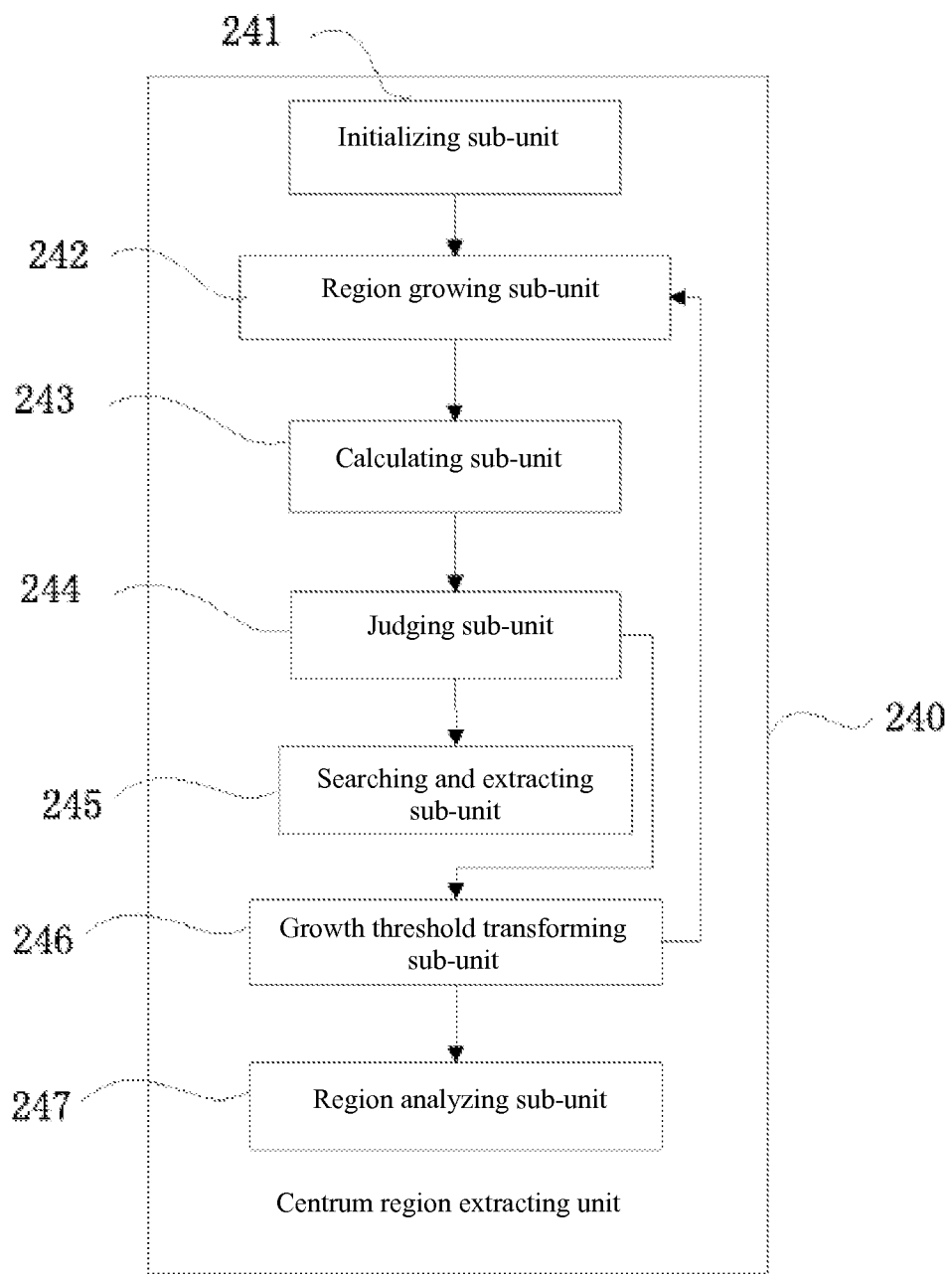
FIG. 3 is a structural diagram for a centrum region extracting unit.

In another embodiment, on the basis that the shape of the centrum is basically fixed, the centrum region extracting unit 240 obtains the centrum region by a region growth method in combination with the area and the shape of the centrum region. As shown in FIG. 3, the centrum region extracting unit 240 may include an initializing sub-unit 241, a region growing sub-unit 242, a calculating sub-unit 243, a judging sub-unit 244, a searching and extracting sub-unit 245 and a growth threshold transforming sub-unit 246. The initializing sub-unit 241 operates to set an initial threshold, a maximum target growth area, and a minimum target growth area. It also assigns the initial threshold to the growth threshold. The region growing sub-unit 242 operates to carry out the region growth based on the growth threshold and the region filling on the grown region. The calculating sub-unit 243 operates to calculate a ratio of the area and perimeter of the filled region, estimate a desired ratio of area and perimeter according to the area of the filled region, and further calculate the difference between the calculated and the desired ratios of area and perimeter. The judging sub-unit 244 operates to judge whether the growth meets a predetermined condition. The searching and extracting sub-unit 245 operates to control and stop the growth when it has met the predetermined condition, and this sub-unit further searches for a minimum difference among the area differences of the filled region, wherein the area of the filled region is between the maximum and the minimum target growth areas. In this way, the growth threshold corresponding to the minimum difference is marked as the optimum one, and the filled region corresponding to the minimum difference is extracted as the centrum region. The growth threshold transforming sub-unit 246 operates to reduce the growth threshold to generate a new one in accordance with a fourth predetermined rule when the growth fails to meet the predetermined condition. This sub-unit then controls the region growing sub-unit 242 to have region growth based on the new growth threshold.

In another embodiment, the centrum region extracting unit 240 further comprises a region analyzing sub-unit 247 which operates to analyze the extracted centrum region and remove some redundant parts from the centrum region according to a fifth predetermined rule.

Figure 4:
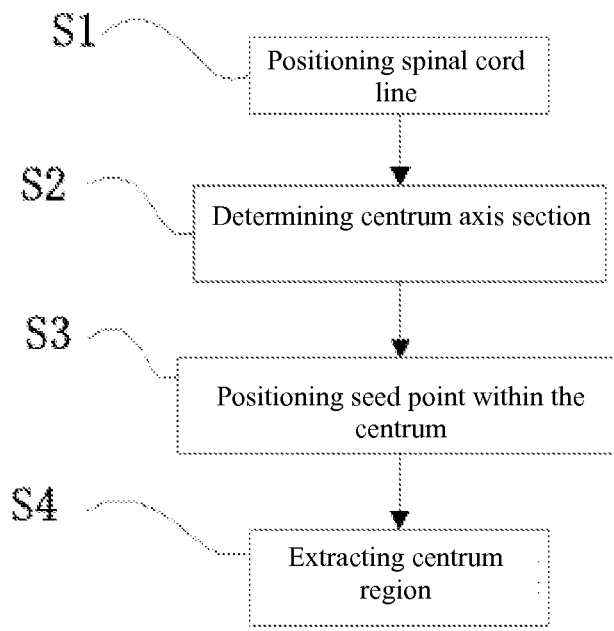
FIG. 4 is a flow chart for extracting spine centrum.

Based on such devices, a spine centrum extracting method is shown in FIG. 4, which may include the following steps (steps S1-S4).

In step S1, a spinal cord line is positioned by using magnetic resonance image data.

In step S2, a centrum axis section is determined according to the spinal cord line.

In step S3, a seed point within the centrum is positioned according to the centrum axis section.

In step S4, a centrum region is extracted on the basis of the seed point within the centrum by using seed region growth.

Figure 5:
FIG. 5 shows a T1-weighted sagittal spine image.

In one embodiment, the spinal cord line is positioned based on the feature of approximately uniform gray scale in the centrum. The spinal cord line is an important feature of the spine image. This is because its gray scale is relatively uniform, and the brightness difference between the spine and its surrounding tissues is basically stable in a T1-, T2- or STIR-weighted image. For instance, the spine seems darker than the surrounding tissues in T1-weighted images, while it seems brighter than the surrounding tissues in T2-weighted images, as shown in FIG. 5. Herein, left and right sides in FIG. 5 respectively corresponds to front and rear sides of the tested subject.

Figure 6:
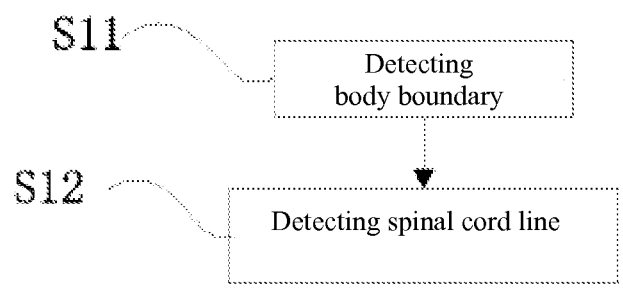
FIG. 6 is a flow chart for positioning a spinal cord line.

In the case that the spinal cord line is substantially in a vertical direction, the process of extracting the spinal cord line is as follows: the body boundary on a first side (e.g., left side) of the tested subject is extracted, the body boundary on a second side (e.g., right side) of the tested subject is extracted, and the spinal cord line is extracted thereafter. For this purpose, the step S1 comprises the following steps (steps S11 and S12) as shown in FIG. 6 in this embodiment.

In step S11, the bilateral body boundaries of the tested subject are detected in his/her magnetic resonance image by using the transition feature between tissues of the tested subject and a background. That is, the transition feature of gray scale between human tissue and background tissue is utilized for extracting the body boundary. As shown in FIG. 5, for example, transition from black to white is present on the left side of the body, while transition from white to black is present on the right side of the body. First-order derivative can be used for detecting such transitions. Since the body boundary substantially extends along a vertical direction, extremum of the first-order derivative is applied in the detection process. A first-order derivative is taken perpendicularly to a body boundary direction (such as a horizontal direction), which can be calculated according to the following expression:

$$\frac{\partial I}{\partial x} * G = I * \frac{\partial G}{\partial x}$$

where I stands for the gray-scale data of an inputted image, $$\frac{\partial}{\partial x}$$

stands for the first-order derivative in x direction (horizontal direction), G stands for the Gauss template, and * stands for convolution.

Figure 7:
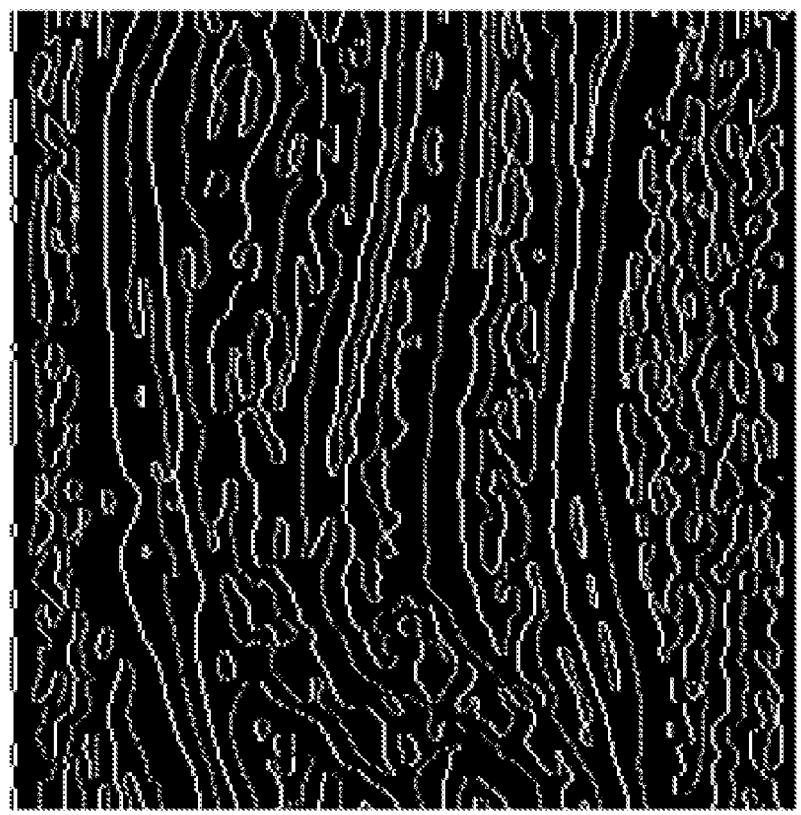
FIG. 7 is a schematic diagram illustrating a set of maximum points or minimum points detected after performing a first-order derivative.
Figure 8:
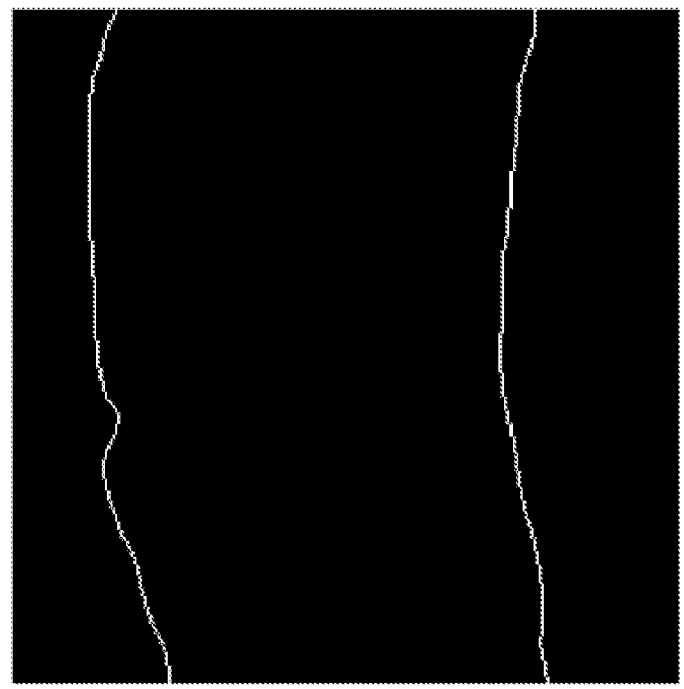
FIG. 8 is a schematic diagram illustrating a detected body boundary.

After calculating the first-order derivative by selecting a proper Gauss template, maximum and minimum points of the first-order derivative are respectively detected in the horizontal direction. The above-mentioned steps are repeated to obtain many maximum and minimum points by changing the location of taking the first-order derivative along the body boundary direction. Some maximum points are connected by line to form a set of maximum points, while a set of minimum points is also obtained in the same way. As shown in FIG. 7, the white points are the maximum values and the grey ones are the minimum values. It can be seen that plurality of sets of maximum and minimum points are formed in the image, in which the sets of maximum and minimum points are respectively used for detecting the body boundaries on the first and the second sides. Since there are too many sets of maximum and minimum points, screening may need to be carried out on them according to a first predetermined rule. Herein, the first predetermined rule can be the line length, the derivative value of each point on the line, and the distance between line and image boundary. The body boundaries on the first and second sides (e.g., left and right sides) are then obtained after screening. As shown in FIG. 8, only one left boundary and one right boundary are left thereon after the screening by the first predetermined rule. Another step S12 is then carried out when obtaining the bilateral body boundaries. Those skilled in the art should understand that the first predetermined rule can also be any other rule besides those disclosed in this embodiment, as long as they can screen out the bilateral boundaries from many boundaries.

In step S12, the spinal cord line is detected according to the tissue width of the tested subject (i.e., distance between bilateral body boundaries) defined by the bilateral body boundaries. In the magnetic resonance image, the spinal cord line has a long and narrow shape, of which the gray scale is apparently different from its surrounding tissues. For instance, the spinal cord line is black in T1-weighted image but is white in T2- or STIR-weighted image. Based on this feature, a second-order derivative sensitive to line structure and required of proper filter scale can be used to detect the spinal cord line. It is noticed that such detection can only be achieved effectively when the filter scale matches with the width of the spinal cord line. Herein, the filter scale can be estimated according to the distance between the body boundaries on the first and second sides. Subsequently, a second-order derivative is taken on the magnetic resonance image by using the estimated filter scale. The expression for calculating the second-order derivative is as follows:

$$I * \frac{\partial^2 G(\sigma)}{\partial x^2}, \sigma = \frac{d_{lr}}{M}$$

where σ stands for the standard deviation of the Gauss template which represents a filter scale and is estimated according to the distance between the body boundaries on the first and second sides, $d_{lr}$ stands for the average distance between bilateral body boundaries, and M is a proportional constant determined by experiments.

Figure 9:
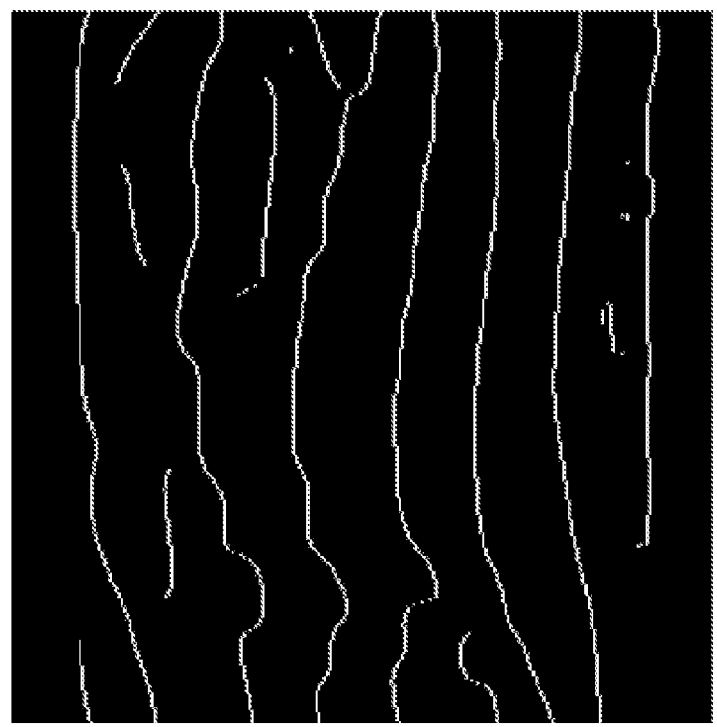
FIG. 9 is a schematic diagram illustrating an extraction result of maximum point after performing a second-order derivative.
Figure 10:
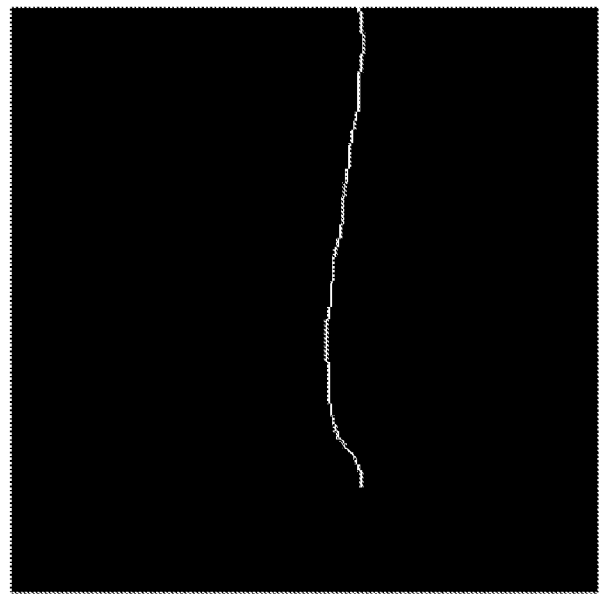
FIG. 10 is a schematic diagram illustrating the spinal cord line obtained through screening.

After filtering by taking the second-order derivative, the extremum of the image is taken, i.e., detect the extremum of the image after the second-order derivative. In the event that it is a T1-weighted image, the maximum value is taken; in the event that it is a T2- or STIR-weighted image, the minimum value is taken instead. In this way, a plurality of sets of extreme points can be obtained by connecting the extreme points by line, wherein an extraction result of the extreme point is shown in FIG. 9. After extracting the extreme point, boundary screening is carried out, and thus the plurality of sets of extreme points are screened according to a second predetermined rule. The second predetermined rule herein (i.e., screening rule) may be based on the length of the spinal cord line and/or the horizontal and/or the vertical location(s) of the spinal cord line in human tissues. In this embodiment, for example, the image is obtained from a lateral side of the tested subject, and thus the spinal cord line is respectively kept right horizontally and up vertically. Thereafter, the spinal cord line is obtained by screening when taking an overall consideration of the length of the spinal cord line. As shown in FIG. 10, the second predetermined rule can be any other rule besides those disclosed in this embodiment, as long as they can screen out the spinal cord line from many boundaries.

In one embodiment, the seed point within the centrum is positioned on the basis that an apparent boundary and even a certain distance are present between the centrum and the intervertebral disk. The process of positioning the seed point is as follows: extracting the centrum axis section, calculating the centrum boundary point, screening the boundary point, and moving the boundary point. In this embodiment, the centrum axis section is first determined according to the spinal cord line using the following procedure: determining a centrum axis according to the spinal cord line and then calculating the gray scale of the centrum axis to form a vector diagram representing the gray scale of the centrum axis (i.e., the centrum axis section). The centrum axis and the spinal cord line which both have the same trend are very close to each other, as a result of which the centrum axis can be obtained by translating the spinal cord line previously determined. The corresponding translation distance can be set based on experiences or be determined according to the width range defined by the bilateral body boundaries. The centrum axis herein is not limited to pass through the center of the centrum. In fact, it can be any line as long as it can pass through all the centrums in the vertical direction, thereby allowing certain positioning error. It is possible to obtain one centrum axis by a single translation or to obtain plurality of centrum axes by multiple translations. Since it is probable to miss the centrum when tanking only a single translation, the purpose of multiple translations herein is to suppress noise. In this embodiment, multiple translations with a plurality of given translation distances are used to obtain multiple centrum axes and further obtain the centrum axis section therefrom. The centrum axis section can be calculated in accordance with the following expression, which calculates a weighted sum of the gray scales of multi-centrum axes to obtain the centrum axis section:

$$\text{spine}(t) = \sum_{n=1}^{S}\left[a_n \cdot I\left(x(t) - \frac{d_{lr}}{M_n}, y(t)\right)\right], \sum_{n=1}^{S} a_n = 1$$

where spine(t) stands for centrum axis section vector, t stands for an index, (x(t), y(t)) stands for the coordinate of the spinal cord line, $a_n$ stands for weighting coefficient, which can be set based on experiences, $M_n$ stands for the multiple of the translation distance with reference to the distance between bilateral body boundaries which can be set based on experiences, and S stands for the number of the centrum axis.

Figure 11:
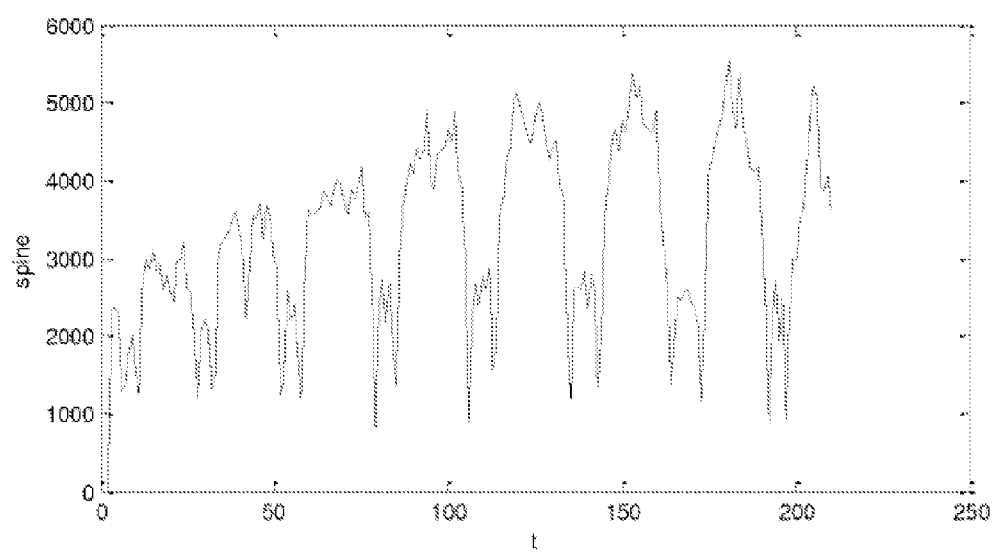
FIG. 11 is a schematic diagram illustrating the gray scale of a centrum axis section.

The extracted centrum axis section is a gray vector, which represents the changes of the approximate gray scale along the centrum axis direction. As shown in FIG. 11, the location where the gray scale changes severely corresponds to the edge of the centrum and the intervertebral disk.

Figure 12:
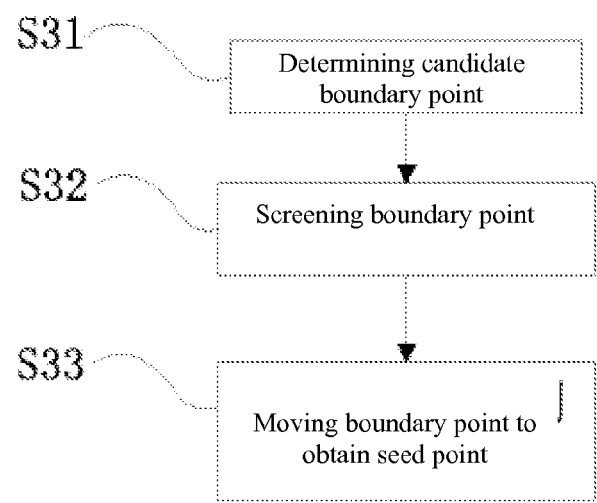
FIG. 12 is a flow chart for positioning a seed point within the centrum.

After determining the centrum axis section, the method for positioning the seed point within the centrum comprises the following steps (steps S31-S33) as shown in FIG. 12.

Figure 13:
FIG. 13 is a schematic diagram illustrating the distribution of centrum axis seed points.

In step 31, a calculation of the variation gradient of the gray scale is performed on the centrum axis section, and the point of which the gradient value is greater than a given threshold is taken as a candidate boundary point of the centrum and the adjacent intervertebral disk. The boundary point can be detected according to gradient features, and this is because the section may have severe change around the centrum boundary points. Through the calculation of a section gradient, those candidate points which meet the demand of |g(t)|>T are selected as the centrum boundary points, wherein g(t) stands for the section gradient, and T stands for a threshold which may be set as T=mean(|g(t)|). The extraction result of the boundary point is shown in FIG. 13, in which the black points are the boundary points.

In step S32, the detected candidate boundary point is screened in accordance with a third predetermined rule so as to obtain the boundary point of the centrum and the adjacent intervertebral disk. There are many redundant boundary points during detection. For example, a plurality of boundary points may be detected for one boundary. This leads to the need of boundary point screening Such screening can be carried out by using the distance feature of the boundary point so that the distance d between any two adjacent boundary points eventually meets the following expression:

$$\frac{d_{lr}}{N_1} \leq d \leq \frac{d_{lr}}{N_2}$$

where $N_1$ and $N_2$ stand for empirical values which can be selected based on experience.

The third predetermined rule can also be any other rule besides the above-mentioned screening rules disclosed in this embodiment, as long as it can screen out some satisfied boundary points from many boundary points to reduce the number of the boundary point.

In this embodiment, extracting the boundary point is for subsequently obtaining as few seed points as possible. When extracting the seed point within the centrum just based on the uniformity, there will be too many candidate points, thus reducing the efficiency of the algorithm.

Figure 14:
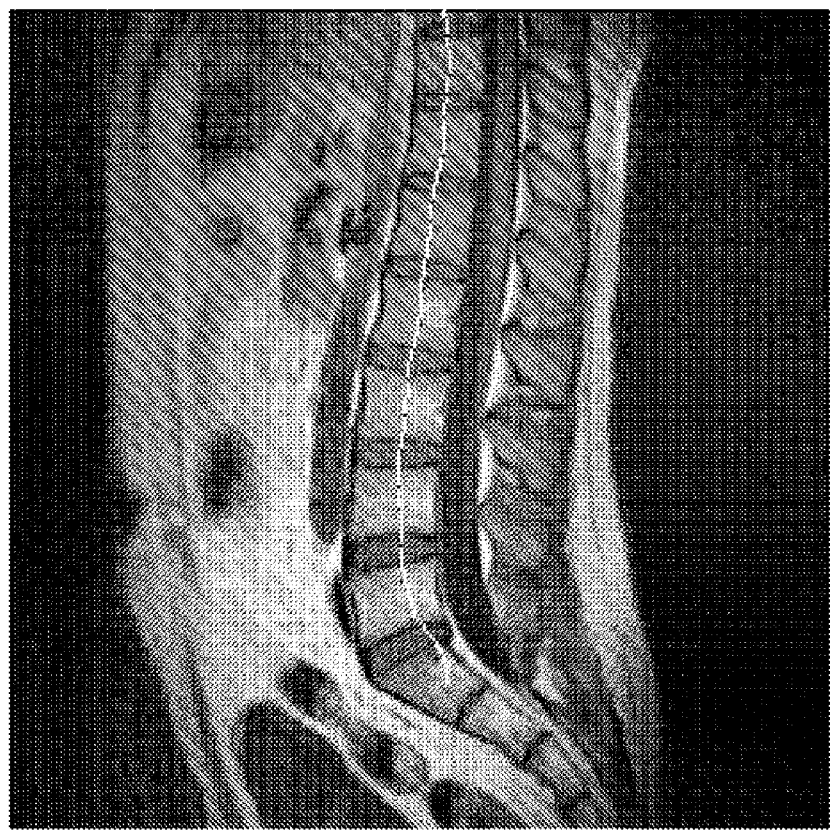
FIG. 14 is a schematic diagram illustrating the distribution of seed points which have moved after screening.

In step S33, the coordinate of the boundary point is moved by a predetermined value along the centrum axis direction. Thereafter, the point corresponding to the generated new coordinate is marked as the seed point within the centrum. For example, the screened boundary point may be moved up or down vertically, which aims at moving the location of the boundary point into the centrum. Such movement is based on the idea that the area of the centrum is larger than that of the intervertebral disk, and thus it is possible to obtain the seed point within the centrum by moving the boundary point slightly, during which the movement distance can be set based on experience. For example, the movement distance can be larger than the vertical width of the intervertebral disk. FIG. 14 is a schematic diagram after the movement during screening, in which many seed points (black therein) have been moved into the centrum.

The variation gradient of the gray scale along the centrum axis is adopted in this embodiment, which gradient represents the change of the gray scale and has no correlation with the absolute value of the gray scale. That is, as long as the gray scale changes, it can be reflected through such gradient. In the magnetic resonance centrum image, the intervertebral disk is always black in the T1-weighted image, while it is white in the T2-weighted image. However, sometimes this kind of feature may not be apparent, indicating only little difference is present between the gray scales of the vertebra and the intervertebral disk. When the seed point is directly extracted by other methods, this problem may always bring about some interference. Nevertheless, whether in T1- or T2-weighted image, there is a clear boundary between the vertebra and the intervertebral disk, which can be detected according to the gradient. As a result, the extracting of the seed point within the centrum in this embodiment is neither affected by the inconsistent gray scale of the centrum or the intervertebral disk, nor by the image weight. Moreover, the extracting of the seed point within the centrum is more accurate for the subsequent centrum region growth.

In another embodiment, a region growth method with a self-adaptive threshold is used for the centrum region growth. In this embodiment, an iterative computation can be performed on the growth threshold by using the area and the shape of the centrum. The coordinate of the grown region meets the following expression:

$$\bigcup_{j=1}^{K} \{(x_i, y_i) \mid |I(x_i, y_i) - I(seedx_j, seedy_j)| < H_j\}$$

where $(seedx_j, seedy_j)$ stands for the coordinate of a j-th seed, $(x_j, y_j)$ stands for an isolated neighborhood set of $(seedx_j, seedy_j)$, K stands for the number of the seed point, and $H_j$ stands for the growth threshold of the j-th seed. Herein, it is important to determine an optimum growth threshold $H_j$.

Figure 15:
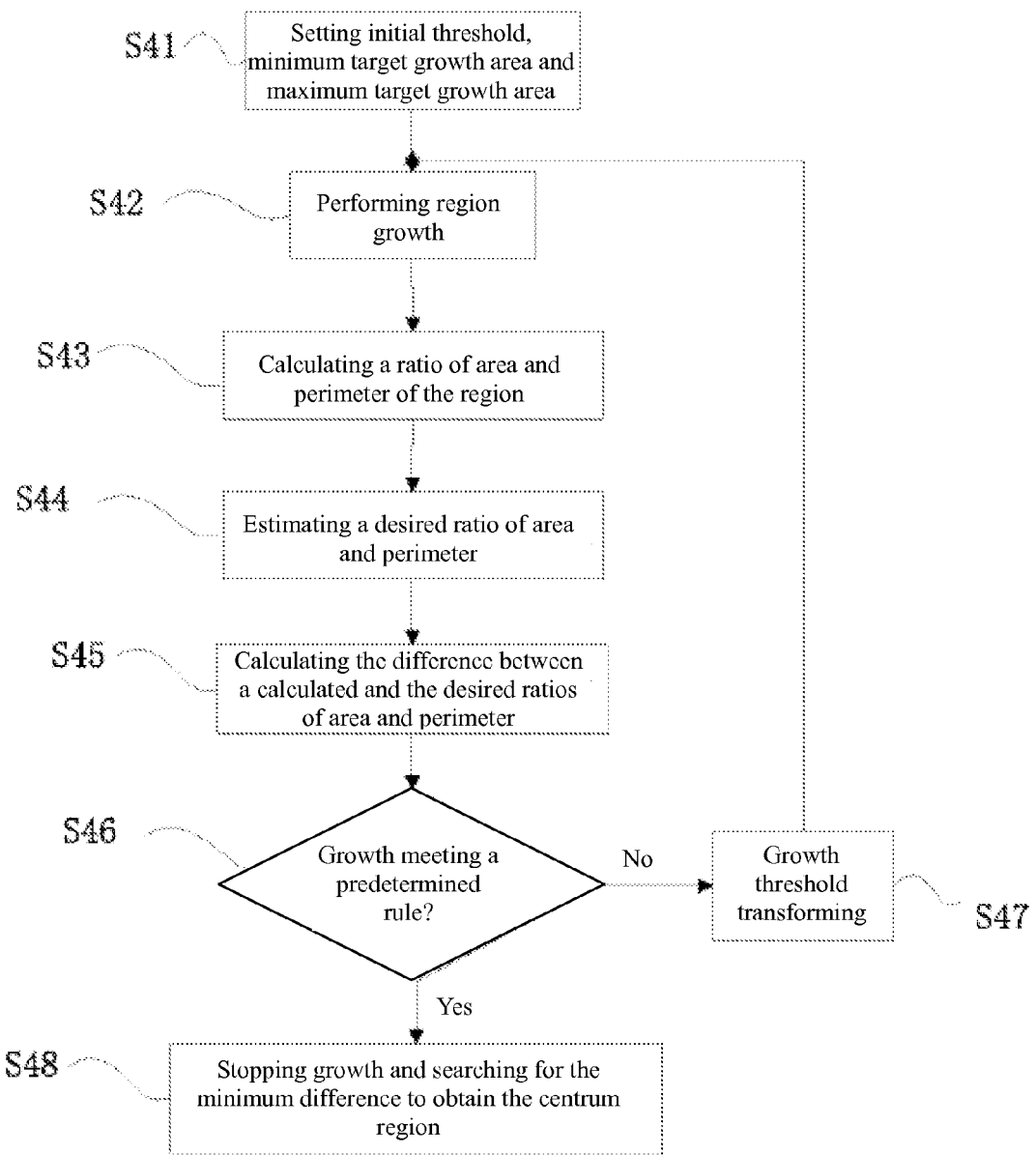
FIG. 15 is a flow chart for extracting a centrum region.

As shown in FIG. 15, when taking a single point as the example, the centrum region extraction by region growth method comprises the following steps (S41-S48).

In step S41, an initial threshold $H_{ini}$, a maximum target growth area ST, and a minimum target growth area SM are set, and the initial threshold $H_{ini}$ is assigned to the growth threshold H. The initial threshold $H_{ini}$ can be a relatively large and fixed value, and it can also be the multiplication of the differences between the maximum gray scale and the minimum gray scale of the centrum axis by a coefficient. SM and ST can be estimated by $d_{tr}$, such as $$SM = \frac{d_{tr}^2}{L_1} \text{ and } ST = \frac{d_{tr}^2}{L_2},$$

wherein $L_1$ and $L_2$ are selected based on experience.

In step S42, the region growth is carried out based on the growth threshold and region filling is then performed on the grown region. Some prior technologies can be used for the region growth and the region filling based on the seed point in this step.

In step S43, a ratio of area and perimeter SP of the filled region is calculated following $$SP = \frac{S}{P},$$

wherein S is the area of the filled region, and P is the perimeter of the filled region.

In step S44, a desired ratio of area and perimeter SPR is estimated according to the area of the filled region. The centrum is basically fixed and approximately square in shape. When supposing the centrum is square in shape, the perimeter can be estimated according to the area S of the filled region, and then the ratio of area and perimeter is calculated again to obtain the desired ratio of area and perimeter SPR, wherein $$SPR = \frac{S}{4\sqrt{S} - 4}.$$

In step S45, the difference between the calculated and the desired ratios of area and perimeter is calculated. In this step, such difference can be the difference value or the ratio of the two.

In step S46, it is judged whether the growth meets a predetermined condition. The predetermined condition can be set as follows: the growth threshold H has been smaller than a given threshold, or the area S of the filled region has been smaller than a given threshold. Provided that the growth meets the predetermined condition, step S48 may be performed, or else step S47 is performed. In step S48, the growth based on this seed is stopped, and a minimum difference is searched among the area differences of the filled region, wherein the area of the filled region is between the maximum and the minimum target growth areas. Subsequently, the growth threshold corresponding to the minimum difference is marked as the optimum one, and the filled region corresponding to the minimum difference is marked as the centrum region based on the seed growth.

In step S47, the growth threshold is transformed. The growth threshold is reduced in accordance with a fourth predetermined rule and the method turns to step S42 in which the region growth is carried out once again based on a new growth threshold. Those steps are performed repeatedly until the growth meets the predetermined condition. The fourth predetermined rule can be set as follows: the growth threshold may be reduced gradually in accordance with a given step size, or the growth threshold may be reduced progressively in accordance with a given curve, or the growth threshold may be reduced irregularly or randomly.

The centrum area cannot be estimated accurately. When the threshold is only determined by centrum area, it is probable to obtain those regions without regular shape and good segmentation effect. Many influencing factors including noise may cause irregular gray scale distribution and undesirable gray scale uniformity of the centrum. The region growing from different gray thresholds may have comparable area but significantly different shapes, while only those regions which nicely match with the vertebra may have regular shapes. As a result, this embodiment considers both the shape and the area information of the centrum so that the grown region is most similar to a real one.

After obtaining the optimum H, i.e., obtaining the centrum region corresponding to a seed point, analysis and judgment is performed on this region for the respective seed point. This is because the number of the seed points obtained previously still has redundancy problems, which mainly include the following two situations:

1) Some seed points are on the intervertebral disk instead of being within the centrum. At this time, even if the above-mentioned region growth is implemented, the region obtained thereafter does not belong to the centrum region.

2) Some seed points are located within a same centrum simultaneously, and the regions growing from them may have overlapped parts.

In order to solve the above-mentioned two problems, the extracted centrum region is further analyzed, and the redundant part is removed from the centrum region in accordance with the fifth predetermined rule. All or part of the following information can be used for removing the redundancy:

consideration of the differences between SP and SPR when each seed point has grown;

consideration of the location information of the region when two seed points next to each other along the centrum axis longitudinally have grown;

consideration of the area differences of the region when two seed points next to each other along the centrum axis longitudinally have grown.

This information can solve the above-mentioned two problems effectively.

Figure 16:
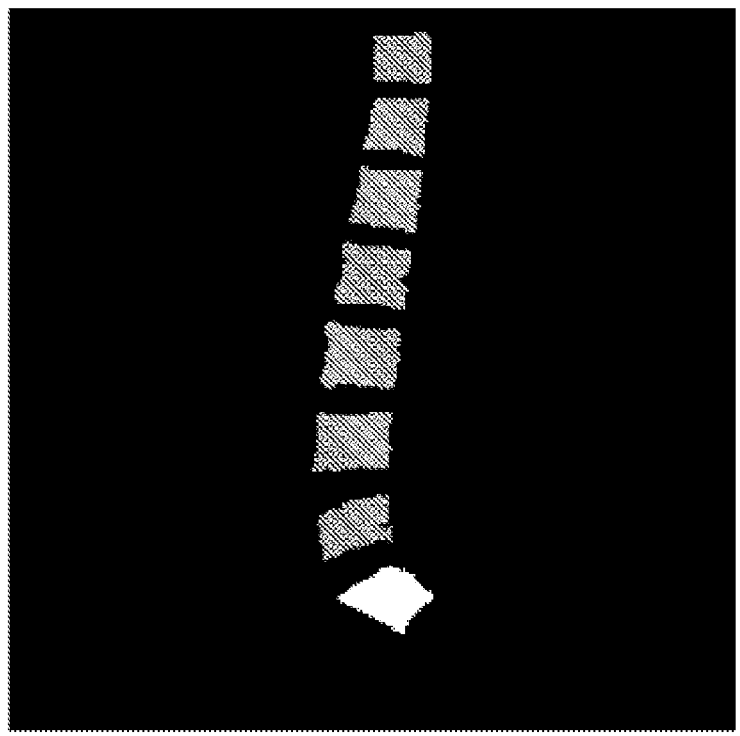
FIG. 16 is a schematic diagram illustrating an extracted centrum region.

The centrum region obtained after region growth as well as region analysis and judgment is shown in FIG. 16.

Those skilled in the art should understand that all or part of the steps mentioned in the above-mentioned embodiments may be used by combination when extracting the spine centrum. For example, prior technology is applied for positioning the spinal cord line, while the technical solution in the embodiment of this disclosure is employed for positioning the seed point within the centrum and for the region growth. Alternatively, the technical solution in the embodiment of this disclosure is employed for positioning the spinal cord line and for the region growth, while prior technology is applied for other steps.

In one embodiment, the control and process system includes a spine intervertebral disk dividing device including: the spine centrum extracting device in any one of the above-mentioned embodiments, a centrum region vertex positioning unit, an intervertebral disk central point positioning unit, and an intervertebral disk central line determining unit. The centrum region vertex positioning unit is configured for positioning the vertex of the centrum region on the extracted centrum region, the intervertebral disk central point positioning unit is configured for calculating a central point of two opposite sides of the intervertebral disk by using the vertices of two adjacent centrum regions, and the intervertebral disk central line determining unit is configured for determining an intervertebral disk central line according to the central point of the two opposite sides.

Figure 17:
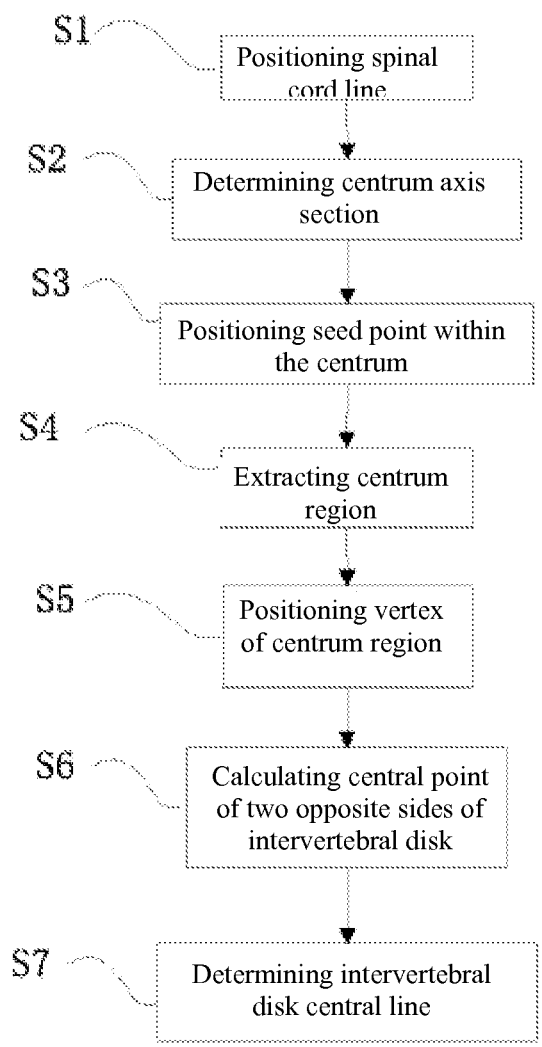
FIG. 17 is a flow chart for dividing a spine intervertebral disk.

Based on the above-mentioned spine intervertebral disk dividing device, a spine intervertebral disk dividing method as shown in FIG. 17 may include the following steps (steps S1-S7).

In step S1, a spinal cord line is positioned by using magnetic resonance image data. In step S2, a centrum axis section is determined according to the spinal cord line. In step S3, a seed point within the centrum is positioned according to the centrum axis section. In step S4, a centrum region is extracted on the basis of the seed point within the centrum by using seed region growth.

In step S5, a vertex of the centrum region is positioned on the extracted centrum region. When positioning the scanning line of the intervertebral disk, it is necessary to determine the expression of the intervertebral disk central line. On the basis of the centrum regions obtained previously, four vertex coordinates need to be detected for each centrum, and the location of the intervertebral disk central point is calculated through the vertex coordinates of two adjacent centrums. The centrum vertex can be extracted by simple helical scanning, wherein four centrum vertices can be obtained when using different scanning directions.

In step S6, a central point of two opposite sides of the intervertebral disk is calculated by using the vertices of two adjacent centrum regions. The midpoint coordinate between the vertex at the left bottom of an upper centrum and the vertex at the top left corner of a lower centrum is the left central point of the intervertebral disk, and the midpoint coordinate between the vertex at the right bottom of an upper centrum and the vertex at the top right corner of a lower centrum is the right central point of the intervertebral disk.

Figure 18:
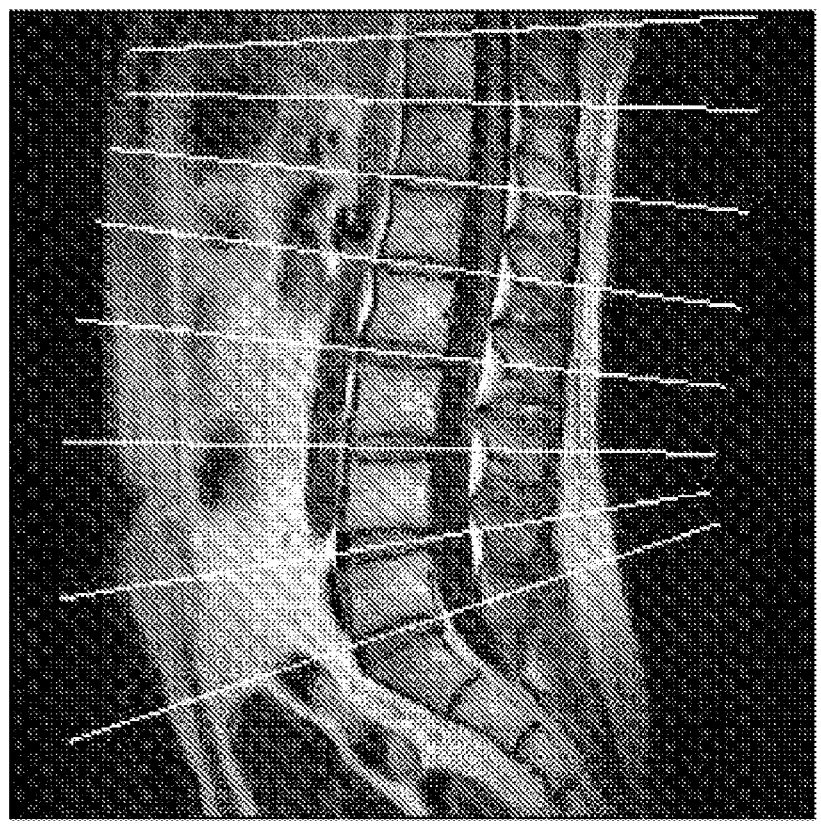
FIG. 18 is a schematic diagram illustrating extracted intervertebral disk central lines.

In step S7, an intervertebral disk central line is determined according to the central point of the two opposite sides. The extracted intervertebral disk central line is shown in FIG. 18.

All or part of the steps provided in this disclosure can be applied for the steps S1-S4 in this embodiment.

Self-adaptive extraction of the centrum and intervertebral disk is implemented based, in one embodiment, on a uniform gray scale within the centrum, a fixed centrum shape, and/or an apparent boundary between the centrum and the intervertebral disk. The extraction results are neither affected by the inconsistent gray scale of the centrum or the intervertebral disk, nor by the image weight. All centrums in the image can be extracted self-adaptively, and the location and the angle of each intervertebral disk central line can further be calculated, which can be effectively applied for the fully automatic positioning of spine intervertebral disk scanning in a magnetic resonance image (MRI). The techniques disclosed herein may be applied in the MRI imaging system with any field intensity.

The above-mentioned implementation has described how to extract the spine centrum or to divide the spine intervertebral disk based on the magnetic resonance image. However, when a tissue image of the tested subject is obtained by any other modes, the methods and/or devices provided in this disclosure can also be used to extract the spine centrum and/or to divide the spine intervertebral disk.

This disclosure has been illustrated in detail with reference to specific implementations mentioned above. However, the disclosure is limited to those specific illustrations. For one of ordinary skill in the art, various simple deductions or equivalents can be made without departing from the concept of this disclosure, all of which should be within the scope of protection of the following claims.

What is claimed is:

1. A magnetic resonance imaging system comprising:
a control system;
a magnet system comprising a magnet that provides a constant main field, a gradient magnetic field coil that generates a gradient magnetic field, a transmitting coil that provides a radio frequency pulse to excite nuclear spin in a subject to be tested, and a receiving coil that detects an echo signal emitting from the subject;
a gradient magnetic field that communicates with the control system and drives the gradient magnetic field coil under the control of the control system, and
a radio frequency system that communicates with the control system, generates the radio frequency pulse and applies an amplified radio frequency pulse onto the transmitting coil under the control of the control system,
wherein the control system comprises a spine centrum extracting device comprising a processing unit for processing magnetic resonance image data of an MR imaging system, the processing unit is configured for:
positioning a spinal cord line by using the magnetic resonance image data;
determining a centrum axis section according to the spinal cord line, wherein the centrum axis section indicates changes of gray scale of multi-centrum axes along a centrum axis direction defined by the spinal cord line;
positioning a seed point within the spine centrum, wherein the seed point is determined according to the centrum axis section; and
extracting a centrum region on the basis of the seed point within the spine centrum by using seed region growth.

2. A magnetic resonance imaging system comprising:
a control system;
a magnet system comprising a magnet that provides a constant main field, a gradient magnetic field coil that generates a gradient magnetic field, a transmitting coil that provides a radio frequency pulse to excite nuclear spin in a subject to be tested, and a receiving coil that detects an echo signal emitting from the subject;
a gradient magnetic field that communicates with the control system and drives the gradient magnetic field coil under the control of the control system, and
a radio frequency system that communicates with the control system, generates the radio frequency pulse and applies an amplified radio frequency pulse onto the transmitting coil under the control of the control system,
wherein the control system comprises a spine intervertebral disk dividing device comprising:
a spine centrum extraction device comprising a processing unit for processing magnetic resonance image data of an MR imaging system, the processing unit is configured for:
positioning a spinal cord line by using the magnetic resonance image data;
determining a centrum axis section according to the spinal cord line, wherein the centrum axis section indicates changes of gray scale of multi-centrum axes along a centrum axis direction defined by the spinal cord line;
positioning a seed point within the spine centrum, wherein the seed point is determined according to the centrum axis section; and
extracting a centrum region on the basis of the seed point within the spine centrum by using seed region growth;
positioning a vertex of a centrum region on an extracted centrum region;
calculating a central point of two opposite sides of the intervertebral disk by using the vertexs of two adjacent centrum regions; and
determining an intervertebral disk central line according to the central point of the two opposite sides.

3. A spine centrum extracting method, which comprises:
positioning a spinal cord line by using magnetic resonance image data;
determining a centrum axis section according to the spinal cord line, wherein the centrum axis section indicates changes of gray scales of multi-centrum axes along a centrum axis direction defined by the spinal cord line;
positioning a seed point within the spine centrum, wherein the seed point is determined according to the centrum axis section; and
extracting a centrum region on the basis of the seed point within the spine centrum by using seed region growth.

4. The method according to claim 3, wherein positioning the spinal cord line comprises:
detecting bilateral body boundaries of a tested subject in a magnetic resonance image by using transition feature between tissue of the tested subject and a background; and
detecting the spinal cord line according to a tissue width of the tested subject defined by the body boundaries.

5. The method according to claim 4, wherein detecting the bilateral body boundaries of the tested subject in the magnetic resonance image comprises:
taking a first-order derivative perpendicularly to a body boundary direction;
detecting maximum and minimum points of a calculated first-order derivative;
changing a location of taking the first-order derivative along the body boundary direction, repeating the derivative and detecting steps, and detecting plurality of sets of maximum points and minimum points; wherein the sets of maximum points are configured for detecting the body boundary on a first side, and the sets of minimum points are configured for detecting the body boundary on a second side; and
screening the plurality of sets of maximum points and minimum points according to a first predetermined rule to obtain the body boundary on the first side and the body boundary on the second side;
wherein detecting the spinal cord line according to the tissue width of the tested subject defined by the body boundaries comprises:
estimating a filter scale according to a distance between the body boundaries on the first and the second sides;
taking a second-order derivative on the magnetic resonance image by using the filter scale;
detecting extremums of the image after the second-order derivative to obtain plurality of sets of extreme points;
screening the plurality of sets of extreme points according to a second predetermined rule to obtain the spinal cord line.

6. The method according to claim 3, wherein determining the centrum axis section according to the spinal cord line comprises:
moving the spinal cord line in accordance with plurality of translation distances to obtain the multi-centrum axes; and
calculating a weighted sum of the gray scales of the multi-centrum axes to obtain the centrum axis section.

7. The method according to claim 3, wherein positioning the seed point within the centrum according to the centrum axis section comprises:
calculating a variation gradient of the gray scale of the centrum axis section, and taking a point of which a gradient value is greater than a given threshold as a candidate boundary point of the centrum and the adjacent intervertebral disk;
screening the detected candidate boundary point in accordance with a third predetermined rule to obtain the boundary point of the centrum and the adjacent intervertebral disk;
moving the coordinate of the boundary point by a predetermined value along the centrum axis direction to obtain a new coordinate and marking a point corresponding to the new coordinate as the seed point within the centrum.

8. The method according to claim 3, wherein extracting the centrum region on the basis of the seed point within the centrum by using seed region growth comprises:
performing a region growth on the basis of the seed point within the centrum to make a coordinate of a grown region meets the following expression:

$$\bigcup_{j=1}^{K} \{(x_i, y_i) \mid |I(x_i, y_i) - I(seedx_j, seedy_j)| < H_j\}$$

where $(seedx_j, seedy_j)$ stands for a coordinate of a j-th seed, $(x_j, y_j)$ stands for an isolated neighbourhood set of $(seedx_j, seedy_j)$, K stands for the number of the seed point, and $H_j$ stands for a growth threshold of the j-th seed.

9. The method according to claim 8, wherein determining an optimum growth threshold of the j-th seed comprises the following steps:
an initializing step for setting an initial threshold, a maximum target growth area and a minimum target growth area, and for assigning the initial threshold to the growth threshold;
region growth step for performing region growth based on the growth threshold;
region filling step for performing region filling on the grown region;
a first calculation step for calculating a ratio of area and perimeter of the filled region;
a second calculation step for estimating a desired ration of area and perimeter according to the area of the filled region;
a third calculation step for calculating difference between a calculated and the desired ratios of area and perimeter;
a judgment step for judging whether the growth meets a predetermined condition; if so, stopping the growth based on the seed and searching for a minimum difference among area differences of the filled region, wherein the area of the filled region is between the maximum and the minimum target growth areas, the growth threshold corresponding to the minimum difference is the optimum growth threshold, and the filled region corresponding to the minimum difference is the centrum region; or else, performing the following step:
a growth threshold transformation step for reducing the growth threshold in accordance with a fourth predetermined rule and performing a loop execution of the region growth step to the judgment step.

10. The method according to claim 9, wherein further comprising after extracting the centrum region:
analyzing the extracted centrum region and removing a redundant part from the centrum region in accordance with a fifth predetermined rule.

11. A spine centrum extracting device, comprising a processing unit for processing magnetic resonance image data of an MR imaging system, the processing unit is configured for:
positioning a spinal cord line by using the magnetic resonance image data;
determining a centrum axis section according to the spinal cord line, wherein the centrum axis section indicates changes of gray scale of multi-centrum axes along a centrum axis direction defined by the spinal cord line;
positioning a seed point within the spine centrum, wherein the seed point is determined according to the centrum axis section; and
extracting a centrum region on the basis of the seed point within the spine centrum by using seed region growth.

12. The device according to claim 11, wherein the processing unit is further configured for:
detecting bilateral body boundaries of a tested subject in a magnetic resonance image by using transition feature between tissues of the tested subject and a background;
detecting the spinal cord line according to a tissue width of the tested subject defined by the body boundaries.

13. The device according to claim 12, wherein the processing unit is further configured for:
taking a first-order derivative perpendicularly to a body boundary direction, detecting maximum and minimum points of a calculated first-order derivative; changing a location of taking the first-order derivative along the body boundary direction, repeating the derivative and the detecting steps, detecting plurality of sets of maximum points and minimum points, and screening the plurality of sets of maximum points and minimum points according to a first predetermined rule to obtain the body boundary on a first side and the body boundary on a second side; wherein the sets of maximum points are configured for detecting the body boundary on the first side, and the sets of minimum points are configured for detecting the body boundary on the second side;
estimating a filter scale according to a distance between the body boundaries on the first and the second sides; taking a second-order derivative on the magnetic resonance image by using the filter scale; detecting extremums of the image after the second-order derivative to obtain plurality of sets of extreme points; and screening the plurality of sets of extreme points according to a second predetermined rule to obtain the spinal cord line.

14. The device according to claim 11, wherein the processing unit is further configured for:
obtaining plurality of the centrum axes after translating the spinal cord line by multiple given translation distances;

obtaining the centrum axis section by carrying out a weighted sum of the gray scales of plurality of centrum axes.

15. The device according to claim 11, wherein the processing unit is further configured for:
calculating a variation gradient of the gray scale of the centrum axis section and take a point of which a gradient value is larger than a given threshold as a candidate boundary point of the centrum and the adjacent intervertebral disk;
screening the detected candidate boundary point in accordance with a third predetermined rule to obtain the boundary point of the centrum and the adjacent intervertebral disk; and
moving a coordinate of the boundary point by a predetermined value along the centrum axis direction to obtain a new coordinate and mark a point corresponding to the new coordinate as the seed point within the centrum.

16. The device according to claim 11, wherein the processing unit is configured for performing a region growth based on the seed point within the centrum to make a coordinate of a grown region meets the following expression:

$$\bigcup_{j=1}^{K} \{(x_i, y_i) \mid |I(x_i, y_i) - I(seedx_j, seedy_j)| < H_j\}$$

where $(seedx_j, seedy_j)$ stands for a coordinate of a j-th seed, $(x_j, y_j)$ stands for an isolated neighbourhood set of $(seedx_j, seedy_j)$, K stands for the number of the seed point, and $H_j$ stands for a growth threshold of the j-th seed.

17. The device according to claim 16, wherein the processing unit is further configured for:
setting an initial threshold, a maximum target growth area and a minimum target growth area, and for assigning the initial threshold to the growth threshold;
performing region growth based on the growth threshold and performing region filling on the grown region;
calculating a ratio of area and perimeter of the filled region, estimating a desired ration of area and perimeter according to the area of the filled region, and calculating difference between a calculated and the desired ratios of area and perimeter;
judging whether the growth meets a predetermined condition;
searching for a minimum difference among area differences of the filled region when the growth meets a predetermined condition, wherein the area of the filled region is between the maximum and the minimum target growth areas, the growth threshold corresponding to the minimum difference is marked as the optimum growth threshold, and the filled region corresponding to the minimum difference is marked as the centrum region; and
reducing the growth threshold to generate a new one in accordance with a fourth predetermined rule and controlling the region growing sub-unit to have the region growth based on the new growth threshold when the growth threshold fails to meet the predetermined condition.

18. The device according to claim 17, wherein the processing unit is further configured for:
analyzing the extracted centrum region and removing a redundant part from the centrum region in accordance with a fifth predetermined rule.

19. A spine intervertebral disk dividing method, wherein comprising:
extracting spine centrum by:
positioning a spinal cord line by using magnetic resonance image data;
determining a centrum axis section according to the spinal cord line, wherein the centrum axis section indicates changes of gray scales of multi-centrum axes along a centrum axis direction defined by the spinal cord line;
positioning a seed point within the spine centrum, wherein the seed point is determined according to the centrum axis section; and
extracting a centrum region on the basis of the seed point within the spine centrum by using seed region growth;
positioning a vertex of a centrum region on an extracted centrum region;
calculating a central point of two opposite sides of the intervertebral disk by using the vertexes of two adjacent centrum regions; and
determining an intervertebral disk central line according to the central point of the two opposite sides.

20. A spine intervertebral disk dividing device, comprising:
a spine centrum extraction device comprising a processing unit for processing magnetic resonance image data of an MR imaging system, the processing unit is configured for:
positioning a spinal cord line by using the magnetic resonance image data;
determining a centrum axis section according to the spinal cord line, wherein the centrum axis section indicates changes of gray scale of multi-centrum axes along a centrum axis direction defined by the spinal cord line;
positioning a seed point within the spine centrum, wherein the seed point is determined according to the centrum axis section; and
extracting a centrum region on the basis of the seed point within the spine centrum by using seed region growth;
wherein the processing unit is also configured for:
positioning a vertex of a centrum region on an extracted centrum region;
calculating a central point of two opposite sides of the intervertebral disk by using the vertexes of two adjacent centrum regions; and
determining an intervertebral disk central line according to the central point of the two opposite sides.

* * * * *